United States Patent [19]

Cragoe, Jr. et al.

[11]  4,187,315

[45]  Feb. 5, 1980

[54] N-ALKYL(AND CYCLOALKYL)OXAMIC ACID AND DERIVATIVES AS INHIBITORS OF GLYCOLIC ACID OXIDASE

[75] Inventors: Edward J. Cragoe, Jr., Lansdale; Frederick C. Novello, Berwyn; Walfred S. Saari, Lansdale, all of Pa.

[73] Assignee: Merck & Co., Inc., Rahway, N.J.

[21] Appl. No.: 950,510

[22] Filed: Oct. 11, 1978

[51] Int. Cl.$^2$ ................. A61K 31/215; A61K 31/195
[52] U.S. Cl. ..................................... 424/305; 424/311; 424/319
[58] Field of Search ....................... 424/305, 311, 319; 560/125; 562/507

[56]  References Cited

PUBLICATIONS

Schuman et al., Biochem-Biophys. Acta, 227, 521 (1971).
Liad et al., Arch. Biochem-Biophys. 154, 68 (1973).
Edmond et al., Brit. J. Pharmac. Chemother, 27, 415-426 (1966).
Stromberg, Material Protection, 4, 60-64 (1965).
Chemical Abstracts, 65:11156e (1966).

*Primary Examiner*—Leonard Schenkman
*Attorney, Agent, or Firm*—Michael C. Sudol, Jr.; Harry E. Westlake, Jr.

[57]  ABSTRACT

N-Alkyl and N-cycloalkyloxamic acid derivatives are disclosed which inhibit glycolic acid oxidase and thus are useful in the treatment and prevention of calcium oxalate urolithiasis (kidney and bladder stone disease).

2 Claims, No Drawings

N-ALKYL(AND CYCLOALKYL)OXAMIC ACID AND DERIVATIVES AS INHIBITORS OF GLYCOLIC ACID OXIDASE

BACKGROUND OF THE INVENTION

Close to 70% of kidney stones are composed partially or predominantly of calcium oxalate. There is no satisfactory drug specific for the treatment of calcium oxalate urolithiasis, nor for prophylactic use by people prone to recurrent attacks of this disease.

Common procedures for treatment of renal lithiasis due to calcium oxalate consist of surgical removal of stones, or control of the diet to restrict intake of calcium and/or oxalate combined with ingestion of large quantities of water to dilute the urine. Attempts at chemotherapy have included the administration of magnesium oxide, orthophosphate, cellulose phosphate, isocarboxazide, thiazide diuretics, allopurinol and succinimide. Limited success has been realized so far by these drug approaches. No drug which specifically inhibits the biosynthetic formation of oxalic acid is available for the treatment of calcium oxalate renal lithiasis.

The immediate metabolic precursor of the majority of the oxalate in human urine is glyoxylic acid. Much of the glyoxylic acid is, in turn, derived from glycolic acid. The enzyme glycolate oxidase (GAO) is known to carry out the oxidation of glycolic acid, through glyoxylic acid, to oxalic acid. Inhibition of this enzyme will therefore lead to a reduction in the concentration of oxalic acid in the kidney and bladder, reducing the probability that calcium oxalate crystallization will occur. Thus inhibitors of glycolate oxidase provide a specific approach to the prevention and treatment of calcium oxalate lithiasis.

SUMMARY OF THE INVENTION

It has been found that N-alkyl or N-cycloalkyloxamic acid derivatives are potent inhibitors of the enzyme glycolate oxidase. They are useful in the treatment of calcium oxalate urolithiasis by virtue of their ability to reduce the metabolic generation of urinary oxalic acid. That is, these compounds diminish or prevent the formation of calcium oxalate kidney and bladder stones.

DETAILED DESCRIPTION

Approximately 70% of all renal calculi contain oxalate as the main anionic component of the matrix. In many but not all patients the condition is associated with a higher than normal level of metabolically produced oxalate. The major immediate precursor of oxalate is glyoxylate. Thus approaches to the reduction of the biosynthetic output of oxalic acid focus on (a.) the prevention of the conversion of glyoxylate to oxalate, and/or (b.) restriction of the production of glyoxylate from its precursors. A major pathway for the biosynthesis of oxalate can be represented as follows:

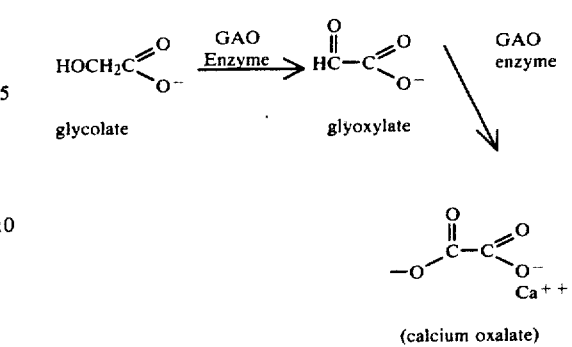

The same enzyme glycolate oxidase participates both in the biosynthesis of glyoxylate and in its oxidation to oxalate. An inhibitor of this enzyme will act to block at two key points in the chain of reactions contributing to the production of oxalate. As a direct consequence of reducing oxalic acid levels in the urine with the compounds of this invention, the formation of oxalate calculi will be reduced or prevented in individuals whose urinary oxalate is primarily of metabolic origin.

The alkyl or cycloalkyl oxamic acid derivatives described herein are potent inhibitors of glycolate oxidase which are effective in reducing the conversion of glycolic acid to oxalic acid in animals. Further, they are of value for the treatment and prevention of renal disease due to calcium oxalate stone formation in the kidney and bladder. In the genetically inherited diseases termed primary hyperoxaluria types I and II, large quantities of oxalic acid are produced metabolically. Crystallization of calcium oxalate, occurring not only in the kidney and bladder but in other tissues as well, frequently results in early death. The compounds of this invention may prove of value in the treatment of these rare, but serious disease states.

The oxamic acid compounds herein described which are useful in preventing the formation of calcium oxalate kidney or bladder stones can be shown by the following formula

Formula I wherein R is alkyl of from 6–12 carbon atoms or cycloalkyl of from 6–12 carbon atoms, and $R_1$ is H, or lower alkyl (straight or branched chain) from 1–6 carbon atoms.

The compounds wherein R is cyclohexyl and $CH_3(CH_2)_7$ are known from CA 62, 15830f (1965) and J. D. Edmond et al., Br. J. Pharmacol. 27, 415 (1966). The compound of Formula I wherein R is cyclooctyl is not known and is herein claimed per se.

The compounds of Formula I can be prepared by a process generally described in the latter reference mentioned above.

For convenience, the process shown in this reference can be depicted by the following equation.

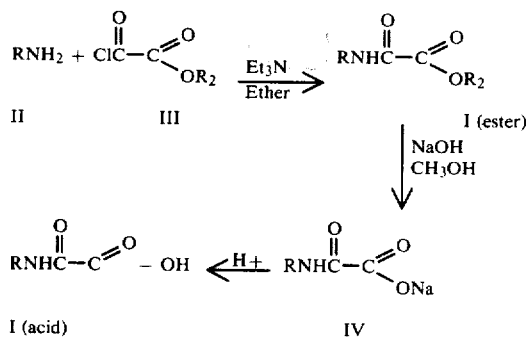

wherein R is as previously described and $R^2$ is lower alkyl (straight or branched chain) from 1-6 carbon atoms.

Thus to prepare the compounds of Formula I one reacts the appropriate amine II with ethoxalyl chloride III in the presence of a tertiary aliphatic amine such as triethylamine, or a second mole of the amine II, in a solvent such as diethyl ether or chloroform to form an oxamic acid ethyl ester (I ester) which is then hydrolyzed by a standard hydrolysis reaction, such as by reaction with a base such as sodium hydroxide in methanol or ethanol, to form a salt (in this case the sodium salt) which itself is acidified by reaction with an appropriate strong acid to yield the desired product I acid.

Included within the scope of the invention are the pharmaceutically acceptable salts of the N-alkyl or cycloalkyl oxamic acids. Thus salts are readily formed by reacting the N-alkyl- or N-cycloalkyloxamic acids with the usual inorganic cations such as sodium, potassium and ammonium. Salts with organic amines such as trimethylamine, triethylamine, n-butylamine and the like are also very stable. The neutralization can be carried out by a variety of procedures known to the art to be generally useful for the preparation of such salts. The choice of the most suitable procedure will depend on a variety of factors including convenience of operation, economic considerations, and particularly the solubility characteristics of the particular free base, the acid, and the acid addition salt.

The N-alkyl or cycloalkyl oxamic acid compounds can be administered to patients (both human and animal) having, or being prone to, calcium oxalate kidney or bladder stone disease by formulating them in a composition in the form of a tablet, capsule or elixir for oral administration. Sterile solutions or suspensions can be used for parenteral administration. About 25 to 500 mg. of said oxamic acid compounds or a pharmaceutically acceptable vehicle, carrier, excipient, binder, preservative, stabilizer, flavor, etc., in a unit dosage form as called for by accepted pharmaceutical practice. The amount of active substance in the composition is such that dosage in the range indicated is obtained. The total daily dose administered to patients having or being prone to calcium oxalate kidney or bladder stone disease will be in the 50 mg to 2000 mg range with a preferred daily dose being 100 mg to 1000 mg of active ingredient. It will be realized by those skilled in the art that the dosage range for any particular patient (animal or human) will depend upon the severity of the disease treated, weight of the patient and any other condition which the physician or other person skilled in the art will take account of.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

Following are example which illustrate the preparation of several compounds and compositions falling within our invention. They should be construed as illustrations of the invention and not limitations thereof.

EXAMPLE 1

N-(n-Octyl)oxamic acid

To a solution of n-octylamine (9.4 g., 0.073 mole) and triethylamine (7.37 g., 0.073 mole) in diethyl ether (100 ml.), cooled in an ice bath, is added dropwise ethyl oxalyl chloride (10 g., 0.073 mole) over 30 minutes. After stirring for 3 hours at room temperature the reaction mixture is filtered, and the filtrate washed with 1.0 N HCl (2×50 ml.), $H_2O$ (2×50 ml.), 1% $KHCO_3$ solution (2×50 ml.), and then $H_2O$ (2×50 ml.). On evaporation a yellow oil is obtained, which is dissolved in petroleum ether (25 ml.). The solution after filtration and evaporation gives 14.4 g. of ethyl N-(n-octyl) oxamate.

Analysis for $C_{12}H_{23}NO_3$:
Calc.: C, 62.85; H, 10.11; N, 6.11;
Found: C, 62,50; H, 10.18; N, 5.73.

When ethyl oxalyl chloride is replaced by n-propyl oxalyl chloride, 2-butyl oxalyl chloride or n-hexyl oxalyl chloride, the corresponding n-propyl, 2-butyl and n-hexyl N-(n-octyl) oxamates are obtained.

To a solution of ethyl N-(n-octyl)oxamate (5 g., 0.022 mole) in methanol (50 ml.) is added slowly NaOH solution (20 ml. of 1 N NaOH diluted with 25 ml. of $H_2O$). After standing for one hour, the mixture is evaporated until the residue is mainly solid. 6 N HCl solution (75 ml.) is added. After stirring for 1 hour the solids are removed by filtration and dried. The yield of N-(n-octyl)oxamic is 3.85 g. (m.p. 89°–93° C.).

Analysis for $C_{10}H_{19}NO_3$:
Calc.: C, 59.67; H, 9.52; N, 6.96;
Found: C, 59.43; H, 9.43; N, 6.97.

By following the above procedure but using corresponding amounts of N-decylamine, cyclohexylamine, or cyclodecylamine, in place of n-octylamine, there is produced a corresponding amount of N-(n-decyl)oxamic acid, N-cyclohexyloxamic acid and N-cyclodecyloxamic acid.

EXAMPLE 2

N-Cyclooctyloxamic Acid

To a solution of cyclooctylamine (12.7 g., 0.10 mole) in chloroform (50 ml.) at 10°-20° C. is added dropwise ethyloxalyl chloride (6.83 g., 0.05 mole) in chloroform (50 ml.) over a period of 30 minutes. After stirring for 2 additional hours at 10° C., the mixture is washed with $H_2O$ (4×50 ml.), and the organic layer dried over $Na_2SO_4$. After filtration and evaporation an oil is obtained (11.3 g.). To the crude ethyl N-cyclooctyloxamate dissolved in ethanol (27 ml.) is added sodium (1.15 g., 0.05 mole) dissolved in absolute ethanol (35 ml.) and the mixture is stirred overnight. Following evaporation, the residue is dissolved in $H_2O$ (41 ml.) with heating, and the solution filtered while hot. The filtrate is acidified with 6 N HCl, and the resulting slurry cooled at ice temperature. The solid obtained by filtration is recrystallized from boiling $H_2O$ (100 ml.) to give N-cyclooctyloxamic acid, m.p. 115°-116° C.

Analysis for $C_{10}H_{17}NO_3$:

Calc: C, 60.28; H, 8.60; N, 7.03;

Found: C, 60.22; H, 8.74; N, 6.97.

When the above process is carried out starting with n-propyl oxalyl chloride, 2-butyl oxalyl chloride or n-hexyl oxalyl chloride, in place of ethyl oxalyl chloride, the corresponding n-propyl, 2-butyl and n-hexyl N-cyclooctyloxamates are obtained in the first step.

EXAMPLE 3

| Dry filled capsules containing 50 mg. of active ingredient per capsule | |
|---|---|
| | Per Capsule |
| N-cyclooctyloxamic acid | 50 mg. |
| Lactose | 149 mg. |
| Magnesium Stearate | 1 mg. |
| Capsule (Size No. 1) | 200 mg. |

The N-cyclooctyloxamic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

What is claimed is:

1. A method of treating or preventing the formation of calcium oxalate kidney or bladder stones, which comprises administering to a patient with, or prone to this disease, an effective amount of a compound of the formula

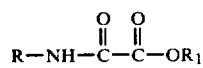

wherein R is alkyl or from 6-12 carbon atoms or cycloalkyl of from 6-12 carbon atoms, $R_1$ is hydrogen or lower alkyl from 1-6 carbon atoms or a pharmaceutically acceptable salt thereof.

2. A method of claim 1 wherein the effective amount of the compound is 50 mg to 2000 mg per day.

* * * * *